United States Patent [19]

Sleytr et al.

[11] Patent Number: 5,028,335

[45] Date of Patent: Jul. 2, 1991

[54] USE OF STRUCTURE WITH MEMBRANE HAVING CONTINUOUS PORES

[76] Inventors: Uwe Sleytr, 10 Parhamerplatz, A-1170 Vienna; Margit Sara, 90/2/24 Vorgartenstr, A-1200 Vienna, both of Austria

[21] Appl. No.: 348,779

[22] Filed: May 8, 1989

Related U.S. Application Data

[63] Continuation-in-part of Ser. No. 174,127, Mar. 28, 1988, Pat. No. 4,849,109, which is a continuation-in-part of Ser. No. 795,349, Oct. 28, 1985, Pat. No. 4,752,395.

[30] Foreign Application Priority Data

Mar. 9, 1984 [AT] Austria .................................. 797/84

[51] Int. Cl.$^5$ ............................................ B01D 69/02
[52] U.S. Cl. .................................... 210/638; 210/656; 210/490; 427/235; 435/176
[58] Field of Search .................. 427/235, 74; 210/490, 210/500.27, 500.37, 500.38, 506, 656, 660, 679, 632, 638; 435/177, 176; 424/85, 94

[56] References Cited

U.S. PATENT DOCUMENTS 4,004,979 1/1977 Avrambas et al. ................... 435/176
4,092,219 5/1978 Lin et al. ...........:................ 435/177 X

*Primary Examiner*—Frank Spear
*Attorney, Agent, or Firm*—Bierman and Muserlian

[57] ABSTRACT

Use of novel membrane crystal lattice structures with continuous pores as ultrafiltration membranes, gas separating organs and separating organs for ion exchange processes, structure for immobilizing molecules, and films as enveloping material for substances.

30 Claims, 4 Drawing Sheets

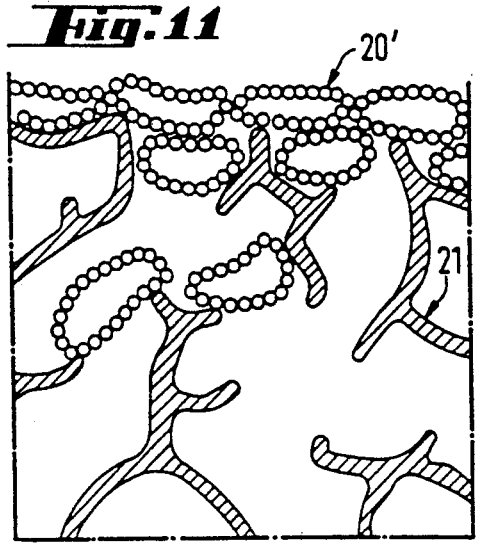
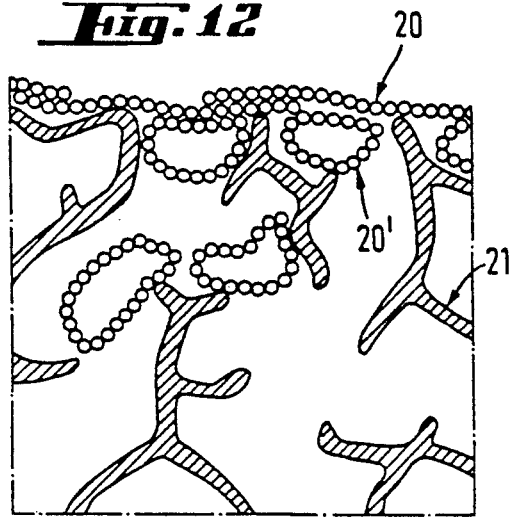
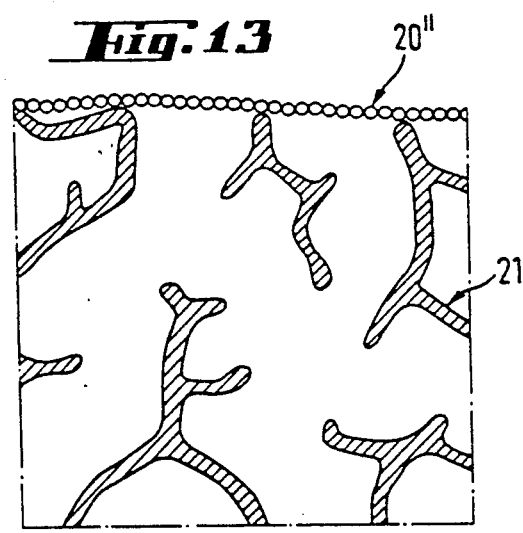
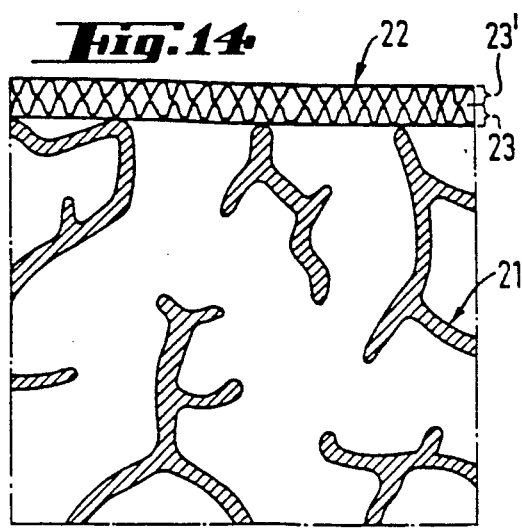
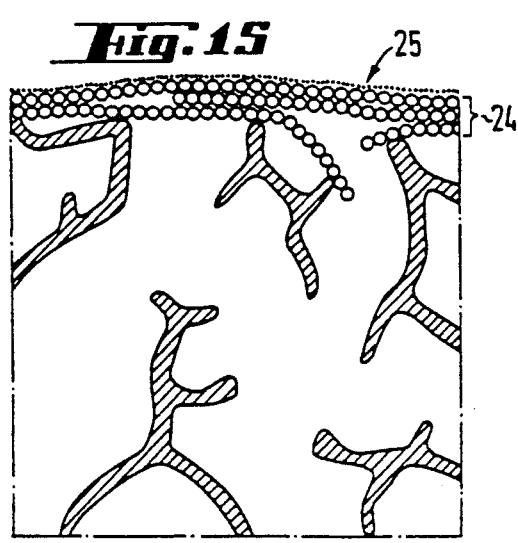
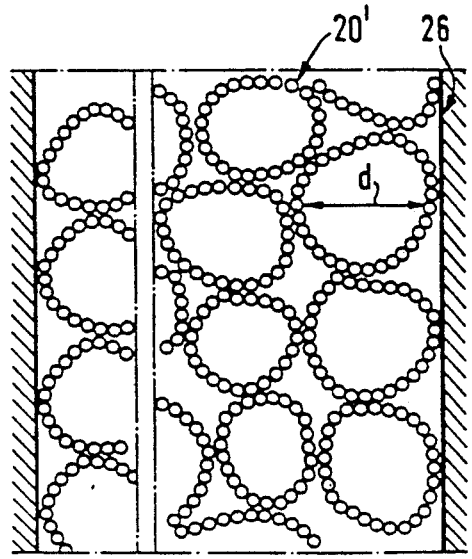

USE OF STRUCTURE WITH MEMBRANE HAVING CONTINUOUS PORES

PRIOR APPLICATION

This application is a continuation-in-part application of copending U.S. patent application Ser. No. 174,127 filed Mar. 28, 1988 now U.S. Pat. No. 4,849,109 issued Apr. 28, 1989 which is a continuation-in-part of application of U.S. patent application Ser. No. 795,349 filed Oct. 28, 1985, now U.S. Pat. No. 4,752,395 issued June 28, 1988.

TECHNICAL DOMAIN

The invention is concerned with a structure which comprises at least one membrane with continuous pores, or which is formed by at least one such membrane, with said pores being particularly within the diameter range of 0.5 to 200 nm, preferably 0.5 to 40 nm (nano-meters). In addition, it concerns a method for the production of this structure, as well as several advantageous applications of said structure.

STATE OF THE ART

Structures with membranes that have continuous pores within a diameter range of 0.5 to 200 nm are, e.g. ultrafiltration membranes used in processes for the fractionation or concentration of mixtures of high-molecular organic substances with different molecular weight. Asymmetrical ultrafiltration membranes are now used in many instances for industrial and semi-industrial purposes; they are comprised of a very thin separating film which is determinative for the mass transfer through the membrane and for the selectively of separation, and which in general is between 100 and 200 nm thick, and of a coarsely porous support layer. The separating films consist of various polymers, preferably of cellulose derivatives or polysulfones. Such ultrafiltration membranes are either phase inversion membranes or composite membranes. In phase inversion membranes, a homogeneous polymer solution is brought into contact with a precipitant, whereupon, at the polymer solution/precipitant contact surface, the membrane is formed, in which latter the coarsely porous support film is joined to the finely porous film. In composite membranes, the separating film and the support film are produed separately and joined together only subsequently.

In the known ultrafiltration membrane, the pore diameter does not have a fixed size, but the diameters of the pores vary, randomly distributed around a mean value. This behavior of the ultrafiltration membrane is characterized by its retention curve. To determine this retention curve, the retention rate (R) of the ultrafiltration membrane during filtration, is determined, in %, for various ideal test molecules (these are spherical molecules in not charged state) with varied molecular weights (MW). The retention curve itself represents an interpolation of these test values and shows the relationship of the retention rate (R) to the logarithm of the molecular weight [log (MW)].

FIG. 1 shows a diagram with the retention curves for three commercially available ultrafiltration membranes, namely:

Curve A for the PSED (Millipore) membrane of Messrs. Millipore, Bedford, Mass. U.S.A.

Curve B for the PSVP 1000 (Millipore) membrane of the same firm, and

Curve C for the PM 30 (Amicon) membrane of Messrs. Amicon, Danvers, Mass. U.S.A.

As can be seen from these retention curves, it is not possible to effect with the aid of these ultrafiltration membranes any sharp separation of molecules with slightly different molecular weights.

A further characteristic value for the performance of an ul/trafiltration membrane is the so-called flow rate. This is the quantity of water which flows through the membrane per $m^2$ and hour at a set pressure difference prevailing between both sides of the membrane. In the known phase inversion, membranes, whose separating films are about 100 to 200 nm thick, the membrane develops considerable resistance to the water flowing through. The flow rate is higher, the higher the number of pores per unit of area of the membrane, or the lesser the effective pore depth, i.e. the length of the canals forming the pores. Additional important quality features of ultrafiltration membranes is also their chemical and/or thermal stability.

DESCRIPTION OF THE INVENTION

The invention has the task of indicating a structure which comprises at least one membrane with continuous pores or is formed of at least one such membrane, wherein said pores are within a diameter range of 0.5 to 40 nm and where, in its application as an ultrafiltration membrane, sharp separation can be realized between molecules with slightly different molecular weights, and with which ultrafiltration membrane it is furthermore possible to attain a higher flow rate than with known ultrafiltration membranes, and which has good chemical and thermal stability.

The task assigned to the invention is solved in the structure according to the invention in that the membrane or the membranes which extend along plane, curved, cylindrical or vesicular surfaces, are in each case constructed of at least one layer of contiguous molecules joined together and thereby arranged according to a crystal lattice, namely protein molecules or protein containing molecules, whereby in these layers, continuous pores arranged according to a lattice remain free between the molecules, and wherein the membranes are linked to or combined within an appropriately porous carrier, or are joined into an unsupported film. In these membranes, the protein molecules or protein containing molecules are advantageously joined into a single layer or into several contiguous layers, in each case arranged according to a lattice, with the continuous protein molecules or protein containing molecules in these layers preferably being joined to each other by non-covalent bonds.

According to an advantageous embodiment of the invention, the structure according to the invention is characterized in that mono- or bifunctional foreign molecules are linked to reactive groups of the protein molecules or protein containing molecules, which advantageously can be carboxyl groups and/or amino groups and/or sulfhydryl groups and/or hydroxyl groups, wherein the structure advantageously exhibits membranes with layers of protein molecules or protein containing molecules, within which foreign molecules are linked to essentially all these molecules at the same reactive places.

According to a further advantageous embodiment of the structure according to the invention, it is characterized in that protein molecules or protein containing molecules of the membranes are intramolecularly covalently cross-linked through bifunctional foreign molecules, and/or in that it has membranes on which contiguous or neighboring protein molecules or protein containing molecules, which belong to the same membranes or to two contiguous or neighboring membranes, are covalently cross-linked to one another appropriately through bifunctional foreign molecules, and/or in which protein molecules or protein containing molecules are cross-linked with the carrier material appropriately through bifunctional foreign molecules.

In yet another advantageous embodiment of the structure according to the invention, it is characterized in that the foreign molecules reach into the zone of the membrane pores recessed between the protein molecules or the protein containing molecules.

Pursuant to a last advantageous embodiment, the structure according to the invention is characterized by membranes, whose protein molecules or protein containing molecules and/or foreign molecules linked to them have dissociable groups, which latter dissociate under working conditions of the structure and can thereby accept predetermined electric charges, depending on these working conditions. Insofar as the type and/or distribution of these dissociable groups at the membrane is concerned, these membranes are advantageously constructed asymmetrically with regard to each surface parallel to the membrane extension.

The invention has the additional task of indicating a method for producing a structure which comprises at least one membrane with continuous pores, and in particular, a method for producing the structure according to the invention.

This problem is solved in the method according to the invention, wherein protein molecules or protein containing molecules, appropriately obtained from cell-envelopes, particularly cell-envelopes of prokaryotic cells, or fragments of layers of such molecules, which are linked contiguous to each other in these layers, are brought into solution or suspension, respectively, in a liquid, appropriately aqueous medium that appropriately contains chaotropic agents, such as guanidine hydrochloride or urea and/or surfactants, and wherein subsequently, appropriately through a reduction of the concentration of the chaotropic agents and/or surfactants and/or through changing the pH-value, conditions are created in the medium at which the protein molecules or protein containing molecules and/or the layer fragments then combine through self-organization into membranes, in which the protein molecules or the protein containing molecules are arranged contiguously according to a crystal lattice, whereby continuous pores arranged between the molecules according to a lattice remain free, and wherein the membranes so formed are placed in, respectively, on a carrier, and wherein, appropriately through treatment with mono- and/or bifunctional foreign molecules, protein molecules or protein containing molecules of the membranes are substituted at their reactive groups, and/or are cross-linked through these reactive groups intramolecularly and/or with each other and/or with the carrier.

To produce the solution or suspension, respectively, of the protein molecules or protein containing molecules and/or layer fragments built up of such molecules, an appropriately aqueous suspension is produced advantageously of cell-envelopes of such a type, as have external layers built up from contiguous protein molecules or protein containing molecules joined to each other and arranged according to a crystal lattice, whereby continuous pores arranged according to a lattice between the molecules in these layers remain free, whereupon, appropriately through adding chaotropic agents and/or surfactants and/or through modifying the pH-value in the medium, said protein molecules or protein containing molecules or fragments of the layers consisting of these molecules are separated from the cell-envelopes, and wherein the remnants of the cell-envelopes are separated from the medium.

Pursuant to advantageous embodiments of the method according to the invention, the separation of the protein molecules or protein containing molecules is advantageously effected through increasing the pH-value from about 7.0 to a value lesser than or equal to 13.0, but in particular to a value lesser than or equal to 9.5, or by reducing the pH-value from about pH 7.0 to a value greater than or equal to 1.0, but in particular to a value greater than or equal to 2.5.

Pursuant to another advantageous embodiment of the invention, the method according to the invention is characterized in that the reduction of the concentration of chaotropic agents and/or surfactants and/or the change of the pH-value to be carried through for inducing the self-organization of the protein molecules or the protein containing molecules and/or the separated layer fragments into membranes, takes place by means of a dialysis.

In a further advantageous embodiment of the invention, the method according to the invention is characterized in that the mono- and/or bifunctional foreign molecules exhibit groups which react with carboxyl groups, amino groups, sulfhydryl groups or hydroxyl groups of the protein molecules or protein containing molecules.

Pursant to another advantageous embodiment of the method according to the invention, the self-organization of the protein molecules or protein containing molecules and/or layer fragments into membranes takes place at a solid-to-liquid phase boundary.

Pursuant to a further advantageous embodiment of the invention, the method according to the invention is characterized in that membranes formed through the self-organization of the protein molecules or protein containing molecules and/or layer fragments, have practically all maximum dimensions in the area of less than 100 $\mu$m, however preferably less than 15 $\mu$m.

In a last advantageous embodiment of the method according to the invention, the placing of the membranes at or in a the carrier, respectively is effected through depositing on the carrier.

Lastly, the invention comprises the following applications according to the invention of the structure according to the invention or of the structure produced pursuant of the method according to the invention, to wit, the utilization of the structure as an ultrafilter, or as a separating organ for a gas separation, or as a separating organ for an ion exchange process;

the utilization of the structure as a carrier for other semi-permeable membranes, which stretch over pores of the membranes of the structure, wherein, appropriately, these other semi-permeable membranes are cross-linked with protein molecules or protein containing molecules of the membranes of the structure through carboxyl groups and/or amino groups and/or sulfhydryl groups and/or hydroxyl groups, directly or through bifunctional foreign molecules. These other semipermeable membranes can advantageously be: monolayers or double layers of native or reconstituted biological membranes, hyperfiltration membranes, appropriately surfactant— or surfactant-like lipoid hyperfiltration membranes or separating organs for an ion exchange process, or separating organs for a pervaporation process, or solution diffusion membranes; utilization as a separating column for column-chromatography, in which the membranes are appropriately shaped as vesicles; utilization as an envelope material for substances, where the envelope material can appropriately be used as a biologically degradable packing material, or as a capsule-envelope for pharmaceutical preparations to be administered orally.

Membranes in which the active filtration layer consists of coherent fragments of the crystalline cell wall surface layer (S-layer). Appropriately the S-layer and the associated peptidoglycan layer of bacillaceae, such as *Bacillus stearothermophilus* PV 72, were used for covalent attachment of invertase to S-layer ultrafiltration membranes. For this purpose, the free carboxyl groups present on the surface of the crystalline lattice were activated with a carboxyl specific reagent, namely 1-ethyl-3-(3-dimethylaminopropyl)-carbodiimide (EDC). Membranes (3 cm² membranes covered with 20 µg crystalline S-layer protein) were transfered to a beaker containing 5 ml of Aqua dest. and after adjusting the pH to 4.75, 50 mg of EDC were added. Activation of the carboxyl groups was effected at pH 4.75 for 1 hour at 20° C. Subsequently, the membranes were washed with ice cold Aqua dest. for removing excess reagent. After inserting the membranes into an ultrafiltration cell (in this case only the surface of the membrane coated with S-layer material was exposed), 2 ml of an invertase solution (2 mg invertase/ml; pH 4.75) were transferred into the ultrafiltration cell, and incubated for 2 hours at 20° C.

During this time, the activated carboxyl groups reacted with the free amino groups of the invertase molecules leading to covalent attachement of the enzyme to the regularly structured S-layer lattice. After removing the membranes from the ultrafiltration cell, they were washed for at least 24 hours with 50 mM of phosphate buffer, pH 7.0. Then, the membranes were transferred into a beaker containing a solution of sucrose (0.15% w/v in 50 mM phosphate buffer, pH 7.0) and incubated for 15 minutes at 37° C. and the activity of the invertase covalently attached to the S-layer lattice was determined by measuring the amount of reducing sugars (glucose and fructose) obtained by enzymatic hydrolysis of sucrose by invertase. Reducing sugars were determined according to the standard method of Somogyl and Nelson and such measurements showed that 1.7 µg of invertase were immobilized per cm² of membrane area.

Vesicles composed of the crystalline cell wall surface layer or appropriately the S-layer and the associated peptidoglycan layer of *Clostridium thermohydrosulfuricum* were used for covalent attachment of peroxidase to vesicular structures. For this purpose, whole bacterial cells were treated with TRITON-X-100 (0.5% in 50 mM of TRIS-HCl buffer, pH 7.2) for 60 minutes at 20° C. After centrifugation at 20,000×g, the pellet was washed several times with TRIS-HCl buffer, and finally centrifuged at 40,000×g. 1 g of wet pellet was suspended in 20 ml of 0.1M sodium cacodylate buffer, pH 7.2, and 0.2 ml of glutaraldehyde (50%) were added. After 20 minutes, the cross-linking reaction was terminated by addition of ethanolamine, and the suspension centrifuged. The pellet was thoroughly washed with distilled water, and resedimented at 40,000×g. 200 mg of this pellet were then suspended in 6 ml of Aqua dest., the pH was adjusted to 4.75, and 50 mg of EDC were added to activate the free carboxyl groups. The suspension was stirred for 60 minutes at 20° C., centrifuged at 20,000×g and washed with ice cold, distilled water, and the pellet was suspended in a peroxidase solution (2 mg of horse radish peroxidase/ml of 0.1M sodium carbonate buffer, pH 8.5). After 18 hours, the suspension was centrifuged at 20,000×g and the pellet was washed at least ten times with 0.1M phosphate buffer, pH 7.0, and centrifuged at 40,000×g. 50 mg of the wet pellet were suspended in 1 ml of 50 mM phosphate buffer, pH 7.0 and 100 µl of this suspension were diluted to 10 ml. 100 µl of this diluted suspension were used for determining the peroxidase activity using $H_2O_2$ as substrate. From activity measurements, it was calculated that 600 µg of peroxidase are attached to 1 mg of S-layer protein of Clostridium thermohydrosulfuricum.

Preparation of S-layer-vesicles from cells of *Desulfotomaculum nigrificans* and treatment with glutaraldehyde was done as described before. For covalent attachement of ferritin to the S-layer lattice, the hydroxyl groups originating from the carbohydrate moiety of the S-layer protein were activated with cyanogen bromide. For this purpose, 0.1 g of wet pellet of S-layer-vesicles was suspended in 5 ml of 0.1M sodium carbonate buffer, pH 10.5, and 50 mg of cyanogen bromide were added. The pH was kept at 10.5 for 20 minutes. Subsequently, the suspension was centrifuged at 40,000×g and twice washed with ice cold distilled water (pH adjusted to 10 with NaOH). Then, the pellet was resuspended in 5 ml of a ferritin solution (2 mg of ferritin/ml of 50 mM phosphate buffer, pH 8.2), and incubated for 16 hours at 4° C. After centrifugation at 40,000×g, the pellet was washed at least five times with 0.1M phosphate buffer, pH 7.0, and then resuspended in distilled water. The electron microscopic examination (using negative staining procedures) showed that one ferritin molecule was bound per morphological unit of the S-layer lattice.

S-layer ultrafiltration membranes in which the active filtration layer consists of coherent regularly structured S-layer fragments or fragments of S-layer still attached to the peptidoglycane from *Clostridium thermosaccharolyticum* were prepared as described before. Dextranase was bound to the hydroxyl groups of the carbohydrate moiety of the S-layer protein. For this purpose, the membranes were transferred to dioxane and incubated for at least 15 minutes. In order to remove the water present in the inner structure of the membranes, treatment with dioxane was repeated at least three times. The membranes were transferred to 5 ml of dioxane containing 80 mg of carbonyldiimidazole (CDl). After 2 hours at 20° C., the membranes were washed with dioxane for removing residual CDl. Then the membranes were inserted into an ultrafiltration cell with a diameter of 25 mm. Thus, only the surface consisting of coherent S-layer fragments was exposed to the protein solution. 5 ml of a dextranase solution (2 mg/ml of 0.1M sodium carbonatebuffer, pH 8.2) were transferred into the ultrafiltration cell and incubated for 4 hours at 20° C. Finally, the dextranase solution was removed and the membranes were washed thoroughly with Aqua dest. and 0.1M phosphate buffer, pH 7.0. Dextranase activity of the membrane was determined by using dextran T-40 as a substrate. 2 ml of a solution of dextran T-40 (5 mg/ml of Aqua dest.) were incubated with the membranes for 30 minutes at 37° C. Subsequently, the amount of reducing sugars were determined using the standard test of Somogyi Nelson. These measurements showed that 2 ug of dextranase were immobilized per cm$^2$ of membrane area.

For preparation of S-layer ultrafiltration membranes using polysulfone as micrporous support, S-layer fragments or fragments of S-layer still attached to the peptidoglycane of *Bacillus stearothermophilus* PV 72 or *Clostridium thermohydrosulfuricum* L 111 (25 μg/ml) were suspended in Aqua dest., and 5 ml of the suspension were used for the production of an ultrafiltration membrane with a total area of 5 cm$^2$, following the procedure described in Example 1 or 2. Polysulfone microfiltration membranes showing a uniform pore size of 0.1 μm were used as microporous supports. After cross-linking of the deposited S-layer fragments on the polysulfone support with glutaraldehyde, small discs with a diameter of 13 mm were punched. Water was removed by incubation in methanol for at least 30 minutes and then the membranes were picked up on filter paper and dried at 20° C. The dried membranes were then transferred into a sputter coater (Polaron instruments) with the surface being coated with the S-layer fragments oriented to the gold target. At a vacuum of $2.10^{-5}$ Torr 200 nm gold was sputtered onto the surface. Then the membranes were wetted with methanol, and transferred to a solution of 30:70/ v:v methanol/chloroform. Membranes were incubated for at least 5 minutes and finally, the polysulfone microfiltration membrane was dissolved with chloroform. The gold layer being in close contact with the S-layer fragments remained as a coherent film and this composite structure consisting of the gold layer and the crystalline S-layer fragments was then transferred onto the surface of a copper grid. In this example, the gold layer functions as a stabilizing support for the S-layer fragments. The coherent S-layer fragments still can be used as a matrix for covalent attachment of foreign molecules such as enzymes or other molecules.

BRIEF DESCRIPTION OF THE DRAWINGS

FIGS. 10 to 16 show sectional views of variant structures.

DESCRIPTION OF THE PREFERRED EMBODIMENTS

The cell envelopes of some prokaryotic cells, in particular of some Bacillaceae, have an external layer, the mass distribution of which, as determined by electron microscopy, has a periodicity which permits the conclusion that the layer has a crystalline structure. This external layer, hereinfollowing called the S-layer (=surface layer), can be separated from the subjacent peptidoclycan contaning layer of the cell-envelope in an aqueous medium by adding chaotropic agents, and brought into solution. As can be determined by biochemical methods, these S-layers in most cases consist of identical molecules, namely protein molecules or protein containing molecules. If the concentration of the chaotropic agents in the solution is reduced, e.g., by dialysis, then small membrane fragments will be formed from these molecules through self-organization, with surface dimensions of up to about 10 to 15 μm, which exhibit the same mass distribution as the original S-layer. These membrane fragments are hereinfollowing called P-membranes. Furthermore, since at an additional increase of the concentration of the chaotropic agents, such P-membranes will decompose again, and will again form as P-membranes during a renewed reduction of the concentration, it is assumed that the P-membranes are built up of layers of contiguous, joined together protein molecules or protein containing molecules arranged according to a crystal lattice, and that the reversibly soluble and reconstitutable lining of the molecules in the P-membranes takes place through non-covalent bonds of these molecules.

Figure 1:
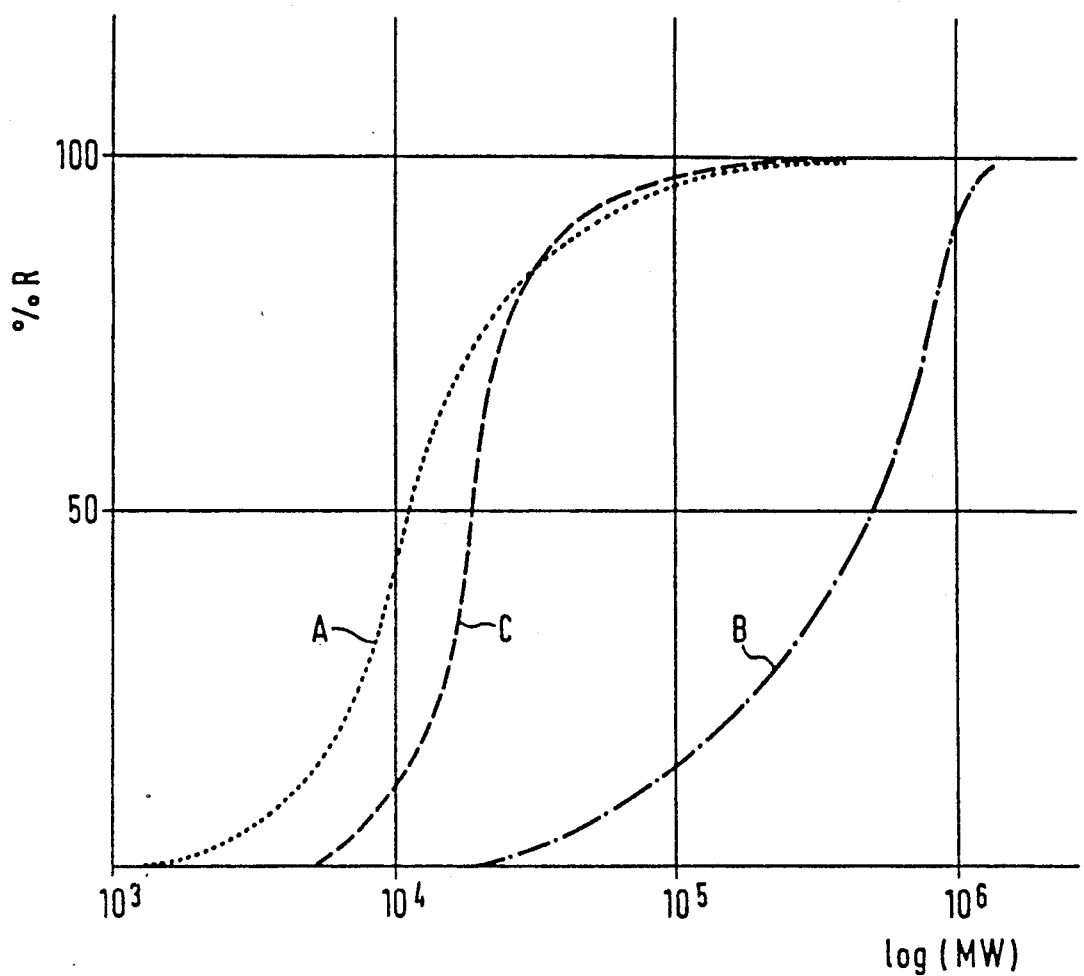
FIG. 1 shows grade efficiency curves for three commercially available membranes.
Figure 2:
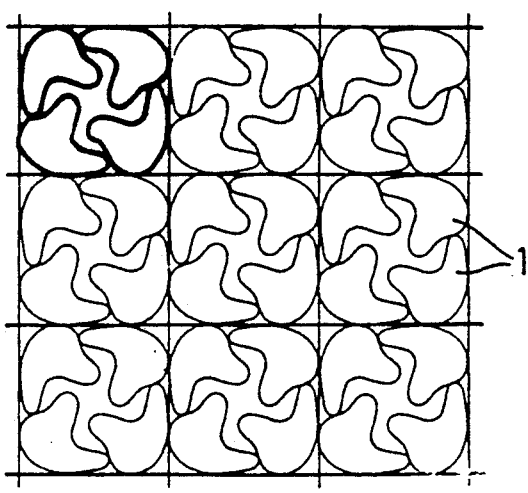
FIGS. 2 to 4 show protein patterns.
Figure 3:
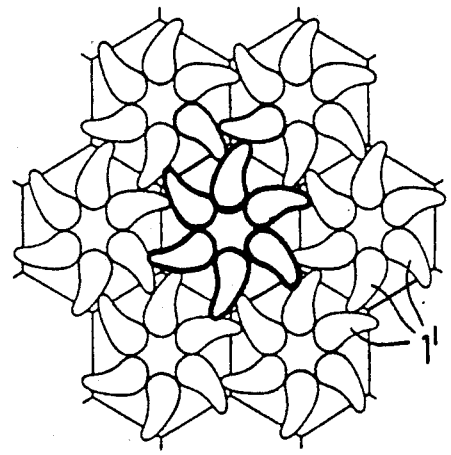
Figure 4:
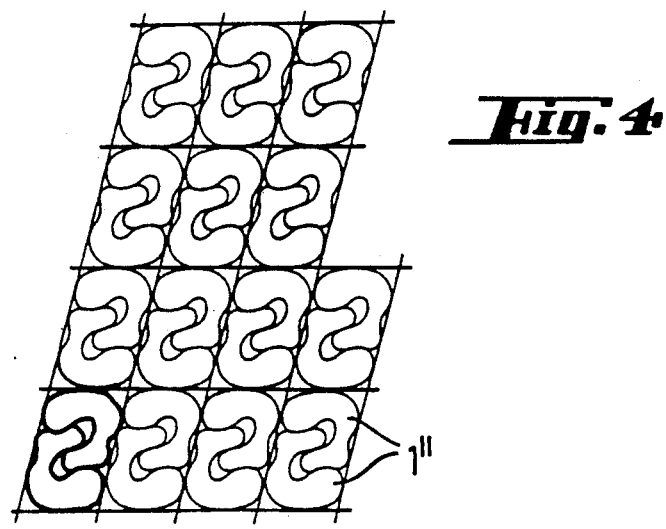

From the mass distribution previously determined, it is possible to recognize the type of lattice, which may be square, hexagonal or oblique. FIGS. 2 through 4 show three types of lattices, in which one may imagine the S-layers and P-membranes, respectively, of the protein molecules or protein containing molecules, respectively, indicated here by 1, 1' and 1'', to be constructed. FIG. 2 shows a square lattice with p4-symmetry, FIG. 3 a hexagonal lattice with p6-symmetry, and FIG. 4 an oblique lattice with p2-symmetry. Based on the information of the mass distribution of the S-layers and/or P-membranes determined by electron microscopy it has been assumed as illustrated schematically in FIGS. 2 through 4 that between the molecules constituting these S-layers and/or P-membranes continuous pores of characteristic form and size are present. This assumption has been confirmed, but it will be discussed only further below.

In the following, with the aid of FIGS. 5 and 7, the production of a structure is described in a first example, for the erection of which such P-membranes are used, and which can advantageously be used as an ultrafilter.

EXAMPLE 1

In this example, one starts with the cells of *Bacillus stearothermophilus* 3c/NRS 1536, the cell-envelope of which is built up of a cytoplasmic membrane, a peptidoglycan containing layer and the S-layer. As is customary in microbiology, the cells are first split open through ultrasonic treatment, the cytoplasmic membrane fragments are disintegrated with the aid of of detergents, and the remaining cell-membrane fragments are cleaned of the components contained in the cell by washing. The S-layers are then separated in an aqueous medium by adding 5M guanidine hydrochloride as chaotropic agent from the peptidoglycan containing layer, and brought into solution. This solution is then separated from the peptidoglycan fragments by centrifugation, and the clear solution is dialyzed against a neutral buffer solution containing 10 mM CaCl$_2$. In the course of this dialysis, in which the concentration of guanidine hydrochloride in the solution is reduced to practically zero and the CaCl$_2$-concentration is increased, the P-membranes are created by self-organization, which exhibit a square lattice structure (p4-symmetry) with a periodicity 14 nm and whose maximum dimensions in the area are about 15 μm, and which are kept in suspension in the aqueous medium through stirring.

Figure 5:
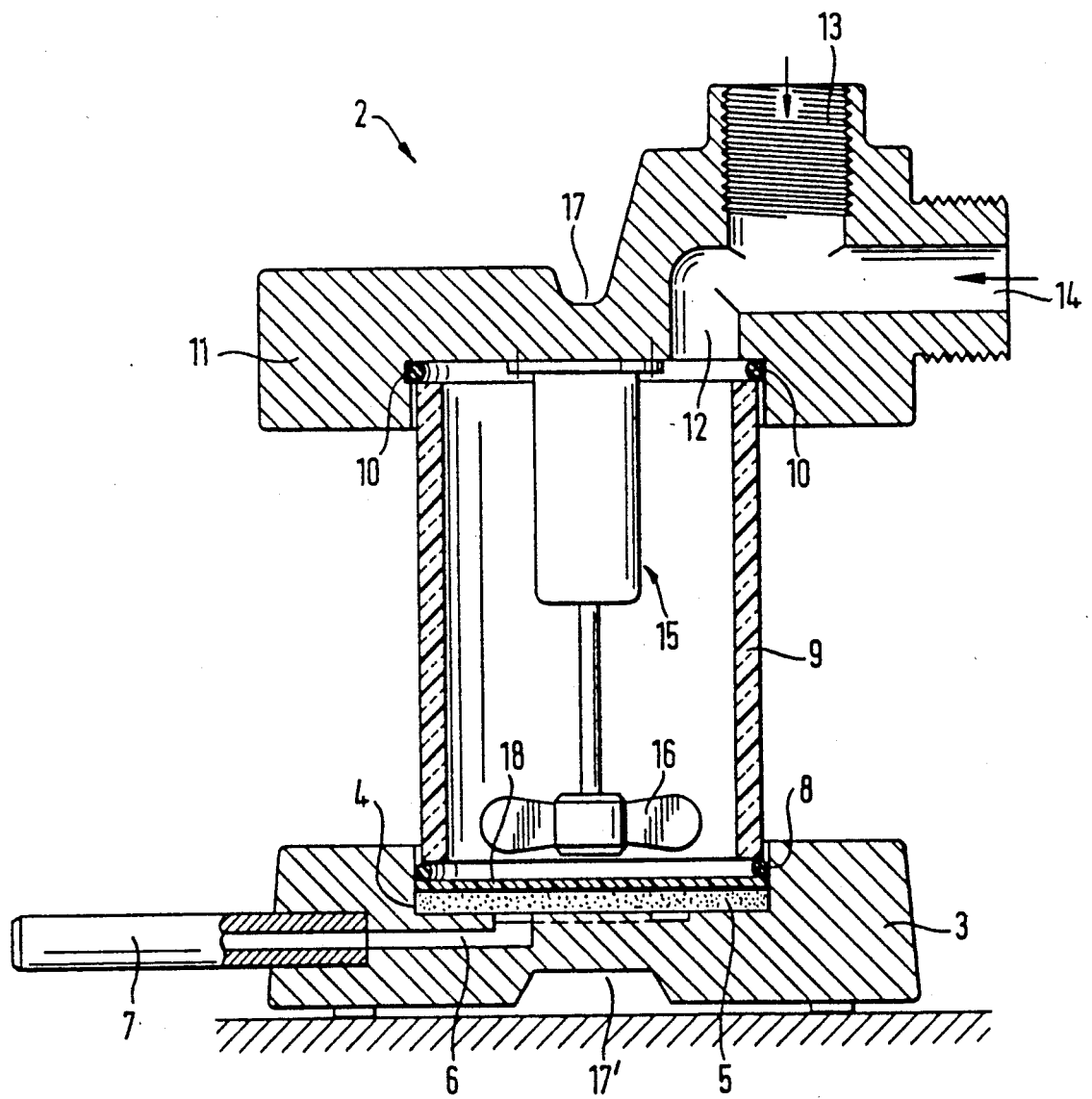
FIG. 5 shows a pressure unit for production of the ultrafilter.

For the production of the ultrafilter, a pressure unit 2, as shown in section in FIG. 5, is used. It is comprised of a bottom part 3, which has a cylindrical groove 4 with a ribbed bottom, in which a porous sinter plate 5 is embedded; the space under the sinter plate 5 is connected to an outlet pipe 7 through an outlet canal 6. A cylindrical wall part of plexiglass is placed on this bottom part 3 by way of an O-sealing ring 8, which wall part is in turn connected to a cover part 11 through a second O-sealing ring 10. In the cover part 11, a supply canal 12 with connections 13, 14 is provided for an inlet pipe or for a pressure gas source, respectively. A magnetic stirring unit 15 is attached to the underside of the cover part 11; with its stirrer 16, it reaches down to the lower edge of the cylindrical wall part 9. For the operation of the pressure unit, the bottom and the cover parts are held together by a clamping device acting at 17 and 17'.

To produce the ultrafilter, a disk-shaped microfilter 18 made by Messers. Nucle/pore, Tuebingen, Federal Republic of Germany, is inserted on the sinter plate 5 in the pressure unit, in order to serve as carrier material for the ultrafilter to be produced. This microfilter 18 consists of a polycarbonate film about 10 μm thick with pores of equal size throughout, with a pore diameter of 0.1 μm. The above-described P-membrane susension is then poured into the cover part 11 through connection 13, in such a quantity that 25 μg of P-membrane are contained in the suspension per cm² area of the microfilter. Thereupon, nitrogen with an overpressure of $0,5.10^5$ Pa is introduced as pressure gas through connection 14, whereby the liquid phase of the suspension is presed through the microfilter 18 and the porous sinter plate 5, and the P-membranes are deposited on the microfilter 18. Subsequently, 3 ml of a 2.0% by volume solution of glutardialdehyde (in 0.1M sodium cacodylate buffer, pH 7.2) are applied to the deposited P-membranes through connection 13. Thereafter, an overpressure of $2.10^5$ Pa is created, which causes the glutardialdeyde solution to be pressed for 20 minutes at 20° C. through the deposited P-membranes and the microfilter 18. The glutardialdehyde has a carbonyl group at both ends and thereby reacts as bifunctional cross-linking agent with two ε-amino groups of the lysine of the protein containing molecules of the P-membranes, namely either intramolecularly, when both ε-amino groups originate from the same protein containing molecule, or intermolecularly, when the two ε-amino groups originate from two different protein containing molecules of the P-membranes.

After repeated washing, the ultrafiltration membrane comprised of the microfilter 18 and the deposited and cross-linked P-membranes are then essentially ready and can be removed from the pressure unit 2. However, the pressure unit 2 with the ultrafiltration membrane thusly produced can also be used directly as an ultrafiltration unit.

For the purpose of determining the retention characteristics of the ultrafiltration membrane produced, filtration tests were carried through with this ultrafiltration unit, at an over-pressure of $2.10^5$ Pa created through introduced nitrogen, for a series of test molecules at pH-values, in which each of the test molecules were not charged electrically, i.e., at their isoelectric point (IEP). The following proteins served as test substances.

| No. | Protein | Molecular weight | IEP |
|---|---|---|---|
| 1 | Myoglobin | 17,000 | 6.6 |
| 2 | Subtilisin | 27,000 | 9.4 |
| 3 | Ovalbumin | 43,000 | 4.6 |
| 4 | Bovine serum albumin | 67,000 | 4.7 |
| 5 | Ferritin | 440,000 | 4.3 |

Figure 6:
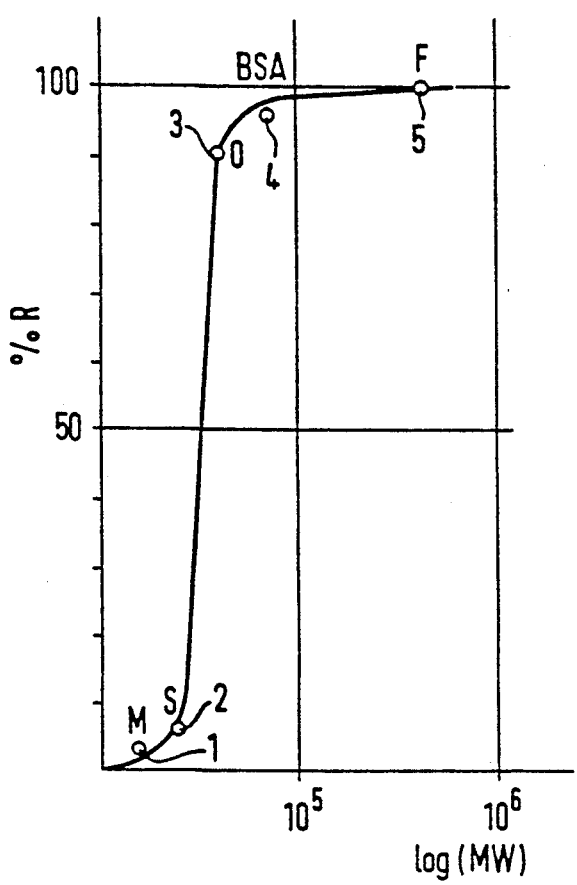
FIG. 6 shows a test value grade efficiency curve.

FIG. 6 shows a diagram with the retention curve interpolated from the test values for the retention rates of these test substances. The retention curve shows a sharp molecular weight cut-off between the retention rates of subtilisin and ovalbumin. This retention curve also proves that the P-membranes possess continuous pores of even size; based on the shape of the retention curve, the pore diameter is assumed to be 4-5 nm.

The flow rate determined with this ultrafiltration membrane at a membrane overpressure of $2.10^5$ Pa is about 480 l/h.m². However, the flow rate depends on the quantity of deposited P-membranes. Thus, it drops to a value of 220 l/h.m² with a deposited P-membrane quantity of 50 μg/cm² membrane surface.

The ultrafiltration membrane produced in this manner has an additional advantageous quality, which is explained below in greater detail:

The free amino groups and carboxyl groups contribute in different ways to the electrical net charge of the S-layer fragments or the uncross-linked P-membranes, respectively, depending on the pH-value of the aqueous medium surrounding them. Up to a pH-value smaller than 9.0, the amino groups produce positive charges, and the carboxyl groups produce negative charges in the range above pH 2.0. At a certain pH-value, i.e., at their isoelectric point (IEP), the negative and positive charges compensate each other, so that the S-layer fragments and the P-membranes will outwardly appear electrically neutral. In the present example, potential positively charged groups of the P-membranes are lost through the reaction of the glutardialdehyde with the ε-amino groups of the lysine of the protein containing molecules of the P-membranes, whereby the IEP of the cross-linked P-membranes is shifted into the acid range and has a value of less than pH 2.0. The negative net charge of the cross-linked P-membranes is in many cases an effective protection against a clogging of the membrane pores in filtrations under physiological conditions.

Figure 7:
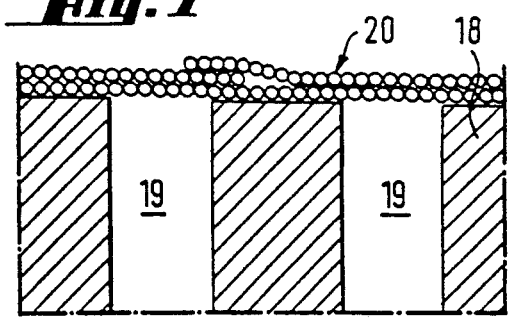
FIGS. 7 and 8 show sectional view of a membrane.

FIG. 7 shows in a partial presentation the ultrafiltration membrane produced according to this example, in schematic section. On the surface of microfilter 18 provided with continuous pores 19, the P-membranes indicated with 20 are deposited and fixed through cross-linking. They are thereby applied in such a quantity that the total surface of the P-membrane quantity is equal to about two or three times the area of the ultrafiltration membranes, so that the P-membranes will on average be superposed in about two layers and thereby will overlap in part.

EXAMPLE 2

Deviating from the method according to Example 1, one starts in this example with cells of *Bacillus stearothermophilus* pV 72. Here, too, the cell-envelopes are comprised of a cytoplasmic membrane, a peptidoglycan containing layer and a S-layer of protein containing molecules. Similar to what has been described in Example 1, a suspension of P-membranes was produced from the cell-envelopes. The S-layer and the P-membranes, respectively, of the cell-envelopes of this bacillus exhibit a hexagonal lattice structure (p6-symmetry) with a periodicity of 18 nm.

To produce a structure usable as an ultrafiltration membrane, a disk-shaped nylon microfilter of type Ultipor $n_{66}$ T of Messrs. Pall, Cortland, U.S.A., 150 $\mu$m thick, is inserted in the pressure unit 2 to serve as carrier. This microfilter has free amino and carboxyl groups in a ratio of 1:1. Similar to the procedure according to Example 1, the P-membrane suspension is applied to the micro-filter in such a quantity that 30 $\mu$g P-membranes are contained in the suspension per $cm^2$ microfilter area, and the P-membranes are deposited on and in the spongy structure of the microfilter, respectively, through application of a membrane overpressure of $2.10^5$ Pa.

Figure 8:
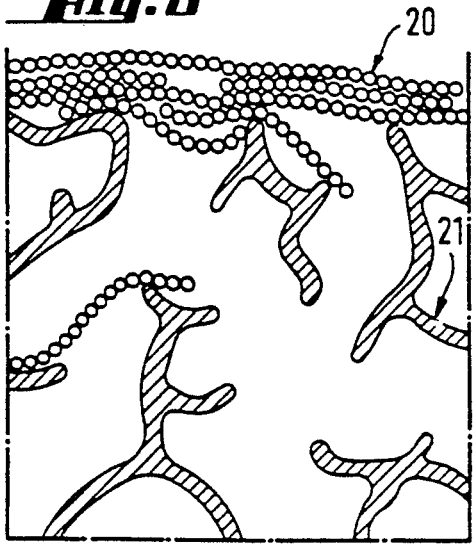

FIG. 8 shows in the partial sectional view the microfilter 21, which has an irregular spongy structure, with the dimensions of the pores left free in a random distribution around a mean value. The deposited P-membranes 20 are also shown. Thereupon, at an overpressure of $2.10^5$ Pa, 1 ml of 0.1% dimethyl suberimidate solution (1M triethanolamine buffer, pH 9.5) is pressed through the P-membranes 20 and the microfilter 21 for 60 minutes at 4° C. The dimethyl suberimidate, as a bifunctional imido ester, thereby reacts like an aldehyde intra- and intermolecularly primarily with the $\epsilon$-amino groups of the lysine of the protein containing molecules of the P-membranes, as well as with the amino groups of the nylon microfilter material. After repeated washing, the ultrafiltration membrane is then ready for use.

Figure 9:
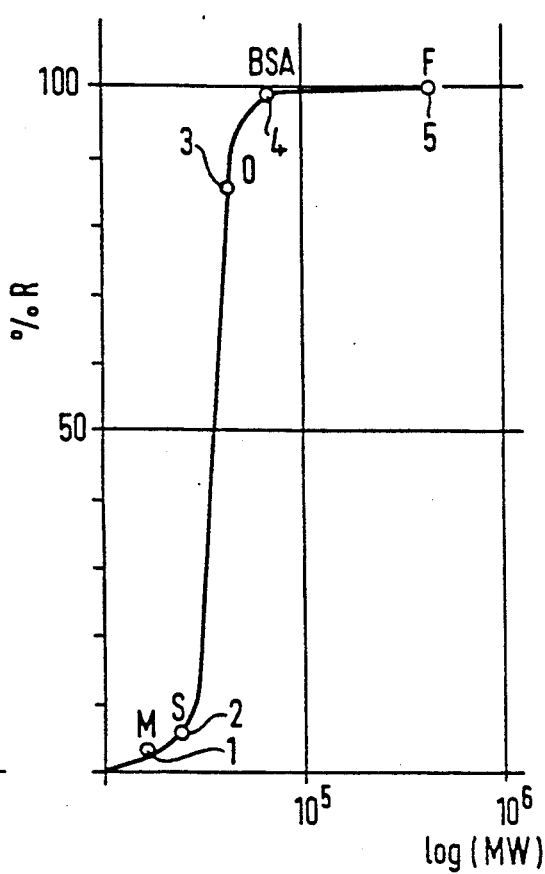
FIG. 9 shows a grade efficiency curve.

FIG. 9 shows the diagram with the retention curve of the ultrafiltration membrane. It shows a sharp molecular weight cut-off, similar to the membrane described in Example 1.

The amidines created during the reaction of the dimethyl suberimidate with the $\epsilon$-amino groups produce a positive charge, in a manner similar as the $\epsilon$-amino group of the lysine, so that the natural net charge of the P-membranes is hardly changed by the cross-linking.

The structures with P-membranes described in the preceding Examples 1 and 2, which can advantageously be used as ultrafiltration membranes, have a high chemical, thermal and mechanical stability through the cross-linking with bifunctional foreign molecules. In particular, they are stable against a proteolytic degradation, they are autoclavable, and can also be used in an acid and alkaline medium (pH 1 to 13), as well as together with highly concentrated chaotropic agents (5M guanidine hydrochloride, 8M urea). Another important property of the structures with P-membranes is their resistance against organic liquids as ketones, alcohols and chlorinated hydrocarbons.

The desired pore diameter of the ultrafiltration membranes is essentially obtained through the selection of the microorganism to be used, the cell-envelopes of which have S-layers with pores of approximately the pore diameter striven for. The desired pore diameter can then be varied through an addition of foreign molecules which reach into the area of the P-membranes. This will be discussed further below.

P-membranes constructed of one molecule layer exhibit layer thicknesses of about 5 to 20 nm, and pore diameter in the range between 1 and 8 nm.

Regarding the production of the P-membrane suspension, it should be noted that through selection of the chaotropic agents and the surfactants, respectively, it is possible to obtain that the S-layer fragments are merely separated from the peptidoglycan containing layer of the cell-envelope fragments, or that the S-layer fragments themselves disintegrate and are brought into solution. For example, if through treatment with 2.5M guanidine hydrochloride only a separation of the S-layer fragments is obtained, a disintegration of the S-layer is achieved with 5M guanidine hydrochloride through rupture of the links between the individual protein molecules or protein containing molecules. A disintegration of the S-layer can also be caused by a substantial change of the pH-value of the solution containing the S-layers; e.g., through lowering the pH-value from about 7.0 to 2.5, or in some cases, by raising it from 7.0 to 9.5.

The surfaces of the P-membranes created by self-organization can be plane, curved, cylindrical or vesicular in form. According to Examples 1 and 2, P-membranes were used, the surfaces of which were essentially plane.

Figure 10:
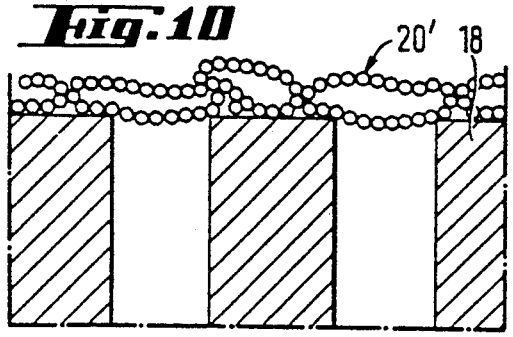

FIGS. 10 and 11 show variants of the structures described in Examples 1 and 2, in which the P-membranes 20' are vesicular in form.

FIG. 12 shows a further variant of the structure according to Example 2, in the production of which vesicular and plane shaped P-membranes 20 and 20', respectively, were used. The vesicular P-membranes were deposited mainly in the pores, while the plane P-membranes were preponderantly deposited on the surface of microfilter 21.

A few additional examples for the cross-linkage of the P-membranes are described below.

Hexamethylene diisocyante reacts at the P-membranes preferably with the amino groups and after they are saturated, with the hydroxyl groups, so that an intermolecular cross linkage can take place through both functional groups. For example, hexamethylene diisocyanate is used in a 1% solution with 5% tetrahydrofuran (triethanolamine hydrochloride, pH 8.0). The reaction time is, e.g., 4 hours at 20° C. N,N'-Diiodoacetyl-hexamethylene diamine attacks sulfhydryl groups at the P-membranes, as do also other bifunctional alkyl halides, yet under suitable reaction conditions, it will also attack the amino groups. In a neutral or weakly alkaline medium, however, this cross-linking agent is specific for the sulfhydryl groups. For cross-linkage, N,N'-diiodo-acetyl-hexamethylene diamine is used preferably in a 0.5% solution (0.1M sodium acetate buffer, pH 7.2). The reaction time is 3 hours at 4° C. 1-Ethyl-3-(3-dimethylaminopropyl)-carbodiimide hydrochloride (EDC).

Carbodiimides such as EDC react in an acid medium with the carboxyl, sulfhydryl and hydroxyl groups at the P-membranes. Sulfhydryl groups—if they are not to take part in the reaction—must be masked beforehand. By blocking the carboxyl groups with EDC, the pH value of the P-membranes is shifted into the alkaline range. 0.1M EDC in distilled water (0.02M NaOH, pH 8.0), for example, is left to react for 18 hours at room temperature.

Several examples for the addition of foreign molecules to the protein molecules or protein containing molecules of the P-membranes are given below, wherein these foreign molecules appropriately affect the pore size of the cross-linked P-membranes:

The P-membranes deposited on a porous carrier, e.g., a microfilter, are coated with a solution of polycationized ferritin (5 $\mu$g polycationized ferritin in 1 ml $H_2O$)

and incubated for 5 minutes at 20° C. As could be determined electron microscopically, one ferritin molecule is linked under these conditions with each protein molecule or protein containing molecule through electrostatic interactions. Through a subsequent cross-linkage with glutardialdehyde analogous to the process described in Example 1, the ferritin molecules are then covalently linked to the P-membranes.

P-membranes applied to a carrier are coated with a 1% solution of osmium tetroxide and incubated for 30 minutes at 20° C. After the excess solution is washed out, the osmium chemically linked in the P-membranes can be established by electron microscopy and with the aid of X-ray micro-analysis. The cross-linking of the P-membranes then takes place according to Example 1.

P-membranes applied to a carrier are treated with a bifunctional cross-linking agent, the bridge-length of which is close to the dimension of the pore-diameter of the P-membrane. The following substances can be considered as bifunctional cross-linkage agents with varying bridge-length.

Tartryl-di-(glycylazide) (TDGA): 1.3 nm bridge-length
Tartryl-di-($\epsilon$-aminocapryol azide) (TDCA): 2.3 nm bridge-length
Bis-methyl-3,8-diazo-4,7-dioxo-5,6-dihydroxydecane bisimidate (DEBE): 1.4 bridge-length
Bis-methyl-4,9-diazo-5,8-dioxo-6,7-dihydroxydecane bisimidate (DOBE): 1.7 nm bridge-length The reaction of TDGA or TDCA, DEBE or DOBE (0.01M in distilled water with 1M triethanol amine, pH 8.0) takes place for one hour at 4° C. or for 30 minutes at 20° C. whereupon cross-linking can take place according to Example 1.

EXAMPLE 3

In this example, a variant of the method according to the invention is described, in which a layer is produced from P-membranes which may have large surface ranges, in particular, dimensions of up to 100 $\mu$m, and which consists of a single-layer P-membrane. To this, a suspension is produced from P-membranes, as described in Example 1, and which was obtained from cell-envelopes of *Bacillus stearothermophilus* 3c/NRS 1536. The S-layers of the cell-envelopes of this bacillus are electrically neutral at their surfaces adjoining the outside of the cell, at which the carbohydrate remnant of the protein containing molecules (glycoproteins) forming these S-layers is exposed, while they have a negative net charge at their other surface. The aforesaid P-membrane solution contains in addition also free protein containing molecules of the layers in solution. A microfilter with an especially smooth surface, such as was also used according to Example 1, is treated at one surface with a soloution of Alcian Blue (0.1% in distilled water) and then dried. The Alcian Blue produces in a neutral medium a positive surface charge on the microfilter surface. The P-membrane solution is then applied to the microfilter under light stirring. Then, induced by the positive surface charge, there takes place at some areas of the microfilter surface, a self-organization into P-membranes of the protein molecules or protein containing molecules still in solution, whereby the negatively charged side of the P-membranes adjoins the positively charged microfilter surface, on the one hand, while, on the other hand, the P-membranes in the suspension, which usually may have maximum surface dimensions of up to 10 $\mu$m, adjoin with their negatively charged side preferably the still free areas of the microfilter surface. To stabilize the thusly formed P-membrane layer, it is cross-linked in a manner analogous to that described in Example 1.

FIG. 13 shows in a partial sectional view of the thusly produced structure, which can also advantageously be used as an ultrafiltration membrane, with microfilter 21, and a P-membrane produced at the solid-to-liquid phase boundary through self-organization, for greater surface expansion. In its application as an ultrafiltration membrane, the structure so produced has the same sharp molecular weight cut-off and retention characteristics as the structure produced according to Example 1.

EXAMPLE 4

Deviating from the method of Example 1, the cells of *Desulfurococcus mobilis*, the cell envelope of which is built up of a cytoplasmic membrane and the S-layer were used. The S-layer was composed of identical proteinaceous subunits arranged in a square lattice structure. Evaluation of the mass distribution of the S-layer lattice by high resolution electron microscopy and digital image reconstruction procedures clearly showed that the pores in the S-layer lattice had a pore size of 20 nm.

The cells were first split open by ultrasonic treatment and the cytoplasmic membrane fragments were disintegrated with the aid of detergents, and the remaining crystalline S-layer fragments were cleaned of the components contained in the cell by washing. For the production of the ultrafiltration membranes, a disk-shaped nylon microfiltration membrane, type Ultipor $N_{66}$ T with a pore size of approximately 0.1 $\mu$m (PALL, Cortland U.S.A.) and with a thickness of 150 $\mu$m was inserted into the pressure unit to serve as carrier. Similar to the procedure of Example 1, a suspension of the crystalline S-layer fragments were applied to the microfiltration membrane in such a quantity that 30 $\mu$g of S-layer protein were contained in the suspension for 1 $cm^2$ of microfiltration membrane area. The S-layer fragments were deposited on and in the spongy structure of the microfiltration membrane, respectively, through application of a membrane overpressure of $2.10^5$ Pa.

Quite generally and in part deviating from the methods described in Examples 1 through 4, it is also possible to use as support surfaces, at which a P-membrane layer is formed, other layers, e.g., peptidoglycan containing layers, pseudomurein layers, lipid layers, polymer layers, gels, metals, glass and the like. When these layers have continuous pores, the size of which is greater than that of the P-membranes, they can serve as a permanent carrier for the P-membrane layers, or they may be auxiliary layers, which are removed after the formation of the P-membrane layer, e.g., by means of organic solvents. The P-member layers separated from auxiliary layers may, appropriately after covalent cross-linking, be applied to a final carrier that is better adapted to the requirements of the intended use of the structure according to the invention, with which carrier they may then also be appropriately covalently cross-linked.

The surface characteristics of the "support surface", such as its hydrophilic or hydrophobic nature, and/or the specific net charge and the charge distribution on the "support surface", permit—similar to the method according to Example 3—an oriented bond of the P-membranes and/or of the protein molecules or protein containing molecules to the "support layer" and thereby promote the formation of the P-membrane-layer. These surface properties should be such, inter alia, that the bonding strength between the "support surface" and protein molecules or protein containing molecules is weak enough so as not to prevent the self-organization of these molecules into P-membranes, which is taking place on this "support surface." This is important for the formation of P-membranes with few disturbances in the crystal lattice.

The above described examples and their variants, respectively, are concerned with structures with P-membranes, in which the protein molecules or protein containing molecules are linked to each other in a single layer. FIG. 14 shows schematically, in a partial, sectional view, a further variant of the structure according to the invention, in which, on a porous microfilter such as was also used according to Example 2, a P-membrane layer is applied consisting of P-membranes 22 built-up in mirror-inverted manner of two layers 23, 23' of protein molecules or protein containing molecules. Each of these two layers of molecules 23, 23' has a different surface topography at its inside and its outside, respectively, and the two layers 23, 23' are appropriately linked to each other in a low free energy arrangement. The two layers 23, 23' can additionally be covalently cross-linked with other, as can the P-membrane 22 with the microfilter 21, respectively.

EXAMPLE 5

Covalent Attachment of Glucose Oxidase to S-layer Ultrafiltration Membranes and Coating the Enzyme with Metal Membranes in which the active filtration layer consists of coherent fragments of the crystalline cell wall surface layer (S-layer) or fragments of S-layer still attached to the peptidoglycane of *Bacillus stearothermophilus* PV 72 were used for covalent attachment of glucose oxidase. For this purpose, the free carboxyl groups present on the surface of the crystalline lattice were activated with a carboxyl specific reagent, 1 ethyl-3-(3-dimethylaminopropyl)-carbodiimide (EDC). Membranes (3 cm$^2$ membranes covered with 20 μg of crystalline S-layer protein) were transferred to a beaker containing 5 ml of Aqua dest. After adjusting the pH to 4.75, 50 mg of EDC were added. Activation of the carboxyl groups was effected at pH 4.75 for 1 hour at 20° C. Then, the membranes were washed with ice cold Aqua dest. for removing excess reagent. After inserting the membranes into an ultrafiltration cell (in this case only the surface of the membrane being coated with S-layer material was exposed), 2 ml of a glucose oxidase solution (2 mg glucose oxidase/ml; pH 4.75) were transferred into the ultrafiltration cell and incubated for 2 hours at 20° C. During this time, the activated carboxyl groups reacted with the free amino groups of glucose oxidase molecules leading to covalent attachment of the enzyme to the regularly structured S-layer lattice forming a monolayer. After removing the membranes from the ultrafiltration cell, they were washed for at least 24 hours with 50 mM phosphate buffer, pH 7.10 and Aqua dest. The membranes were carefully dried and transferred to a Sputter Coater (Polaron Instruments) for depositing a gold layer on the immobilized glucose oxidase. At a vacuum of $5.10^{-2}$ TORR, gold was deposited for 2 minutes at a current of 20 mA. The composite structure obtained by this procedure consisted of an S-layer ultrafiltration membrane, the immobilized enzyme and a metal layer deposited on the enzyme monolayer. This composite structure allows a direct electron transfer from the glucose-oxidase to the metal coating (e.g., electrode or sensor surface). In a similar way other oxidases can be immibolized and metalcoated for achieving direct electrone transfer.

Several Additional Advantageous Applications of the Structure According to the Invention, which are Commercially Significant In addition to an application as ultrafiltration membrane, the structure according to the invention can also be utilized advantageously as separating organ for a gas separation or as separating organ of an ion exchange process.

In further, advantageous applications, the structure according to the invention serves as carrier for other semi-permeable membranes which stretch over the pores of the P-membranes of the structure. These other semi-permeable membranes can be hyperfiltration membranes, in particular mono- or bimolecular hyperfiltration membranes. Such hyperfiltration membranes, particularly surfactant—or surfactant-like lipoid hyperfiltration membranes are generally only 2 to 6 nm thick and are particularly fragile. Hyperfiltration membranes are utilized especially in the areas of seawater desalination, sewage treatment, separation of mixtures of organic liquids, in particular for hydrocarbon separation through pervaporation or for separating optical antipodes by means of chiral separating layers.

FIG. 15 shows in partial sectional view a structure according to the invention, the production of which has been described in Example 2 (see FIG. 8), on the P-membrane layer 24 of which the hyperfiltration membrane 25 has been applied. In the utilization of the structures according to the invention as carriers of hyperfiltration membranes, the filtering or the separating action, respectively, is essentially determined by the hyperfiltration membrane. Defects, such as small holes or the like in the P-membrane layer 24 are not necessarily troubling. The cross-linked P-membrane layer is particularly suitable as a carrier for the hyperfiltration membranes, since they have sufficient mechanical stability to so stretch over or fill up pores and rough surfaces of the customary carrier layers of ultrafiltration membranes that the fragile hyperfiltration membranes, especially cross-linked monolayers, can be consistently mounted or separated. Furthermore, the P-membrane layers are sufficiently thin and have a high porosity to ensure an adequately high rate of flow in combination with the hyperfiltration membranes.

A particularly smooth surface of the P-membrane layer is obtained especially with the aid of the following method. Similar to what has been described in Example 1, a P-membrane layer is produced and cross-linked on a polycarbonate carrier with a very smooth surface. The polycarbonate carrier is then dissolved in chloroform, whereby a cohesive P-membrane layer 5-100 nm thick is left, which is then deposited with its original very smooth bottom side up onto another porous carrier. On this very smooth exposed surface of the P-membrane layer, the hyperfiltration membrane is then deposited and appropriately cross-linked with the P-membrane layer.

Compounds of a P-membrane layer and a hyperfiltration membrane can also be produced, in that on a hyperfiltration membrane that has a defined surface net charge serving as "support surface"—e.g., analogous to what has been described with the aid of Example 3—a P-membrane layer is formed and the latter is appropriately cross-linked with the hyperfiltration membrane.

For a covalent cross-linking between the hyperfiltration membrane and the P-membrane layers, those reactions may be considered above all, in which carboxyl, hydroxyl, amino and sulfhydryl groups participate. With P-membranes of glycoprotein and single-layer hyperfiltration membranes with sugar residues, carbohydrate chemical reactions may also be used.

Compounds of a P-membrane layer and a hyperfiltration membrane can furthermore serve themselves as carrier or "support surface" for additional hyperfiltration membranes or P-membrane layers. Such multilayer compounds can also be cross-linked in the plane of the single layers or also between the single layers through covalent bonds. The formation of a sandwich compound consisting of two hyperfiltration membranes at both sides of a P-membrane layer permits the interleaving of foreign molecules, such as enzymes or charge carriers, which can substantially influence the behavior of such a sandwich compound.

The aforesaid compounds or multilayer compounds, respectively, can advantageously also take the form of closed vesicles, in the production of which one may start with a "starting vesicle" consisting of a hyperfiltration membrane or of a P-membrane layer.

In a further advantageous application, the structure according to the invention is used as separating column for column chromatography. FIG. 16 shows schematically in a partial sectional view such a chromatography column 26, in which vesicular, appropriately intra- or intermolecularly cross-linked P-membranes 20' with an inside diameter d in the range of 1 to 3 μm have been filled in. The substances to be separated are fed in at the top of the column. After the substances are passed through and eluted, the larger molecules emerge at the lower end of the chromatography column earlier than the smaller molecules, with the chromatography showing a sharp fractionation in the range of the pore-size of the P-membranes.

According to an advantageous variant, the flow rates through the separating column can be increased in that the P-membrane vesicles 20' are combined covalently cross-linked in morphologically defined and mechanically stable aggregates. To produce these aggregates, a dense pellet (sediment) of P-membrane vesicles is quick-frozen in a thin layer, pulverized into small fragments under liquid nitrogen and subsequently freeze-substituted in a mixture of methanol and glutardialdehyde at, e.g., $-80°$ C., whereby the cross-linking takes place with the aid of the glutardialdehyde. The aggregates so obtained can be fragmented still further, sifted by size categories, with only specific size categories of the aggregates to be used for filling the separating column. In addition, either before or after the column is filled, the aggregates can be transformed into buffers and/or chemical or enzymatic changes of the aggregates can be effected.

In a last advantageous application, the structure according to the invention is used as envelope material for the most varied substances. This envelope material may be a cross-linked P-membrane layer which, as described is produced on an auxiliary layer or "support surface", whereupon the auxiliary layer is appropriately removed. The films thusly produced can advantageously be used as packaging material and as such have the advantage in that they are appropriately biologically degradable, and the degradation speed can be influenced by the type and the degree of the covalent cross-linking.

P-membrane layers of this type can finally also find application as capsule-envelopes for pharmaceutical preparations administered orally, whereby the desired release of the content is caused only by the proteolytic degradation in specific sections of the digetive tract. By a selective chemical change of the P-membrane layers of the envelope membranes, their speed of degradation and thereby the time of release of the capsule contents can be determined. The release of the capsule content may take place already before the P-membrane layer is dissolved, for which it is controlled by the pore-size. Moreover, pH-effects can also induce the release.

What we claim is:

1. A substance enveloped in a film of a structure comprising at least one membrane extending along a plane, curved, cylindrical or vesicular surface consisting essentially of at least one layer of identical protein containing molecules, which molecules are arranged to form a crystal lattice having a lattice constant of 1 to 50 nm.

2. A pharmaceutical enclosed in a capsules envelope of a structure comprising at least one membrane extending along a plane, curved, cylindrical or vesicular surface consisting essentially of at least one layer of identical protein containing molecules, which molecules are arranged to form a crystal lattice having a lattice constant of 1 to 50 nm.

3. In a method of immobilizing molecules on a carrier, the improvement comprising using as the carrier a structure comprising at least one membrane extending along a plane, curved, cylindrical or vesicular surface consisting essentially of at least one layer of identical protein containing molecules, which molecules are arranged to form a crystal lattice having a lattice constant of 1 to 50 nm.

4. The process of claim 3 wherein the membrane has pores with a diameter of 0.5 to 40 nm.

5. The process of claim 3 wherein the molecules immobilized on the carrier are at least one member of the group consisting of proteins and peptides.

6. The process of claim 3 wherein the molecules immobilized on the carrier are at least one member of the group consisting glycoproteins and glycopeptides.

7. The process of claim 3 wherein the molecules immobilized on the carrier are at least one member of the group consisting of polysaccharides, oligosaccharides and sugars.

8. The process of claim 3 wherein the molecules immobilized on the carrier are lipids.

9. The process of claim 3 wherein the molecules immobilized on the carrier are lipopolysaccharides.

10. The process of claim 3 wherein the molecules immobilized on the carrier are enzymes.

11. The process of claim 3 wherein the molecules immobilized on the carrier are antigens.

12. The process of claim 3 wherein the molecules immobilized on the carrier are antibodies.

13. The process of claim 3 wherein the molecules immobilized on the carrier are lektins.

14. The process of claim 3 wherein the molecules immobilized on the carrier are haptens.

15. The process of claim 3 wherein the molecules immobilized on the carrier are nucleic acids.

16. The process of claim 3 wherein the molecules immobilized on the carrier are colors.

17. The process of claim 3 wherein the molecules immobilized on the carrier are metal compounds.

18. The process of claim 3 wherein the molecules immobilized on the carrier are transmitter molecules.

19. The process of claim 3 wherein the molecules are enzymes and the structure is used as ELISA or enzyme membranes.

20. The process of claim 3 wherein the molecules are at least one member of the group consisting enzymes, antigens, antibodies, lektins, haptens, nucleic acids, colors, metal compounds, Biotin, Avidin and transmitter molecules and the structure is used as diagnostic reagent.

21. The process of claim 3 wherein the molecules are at least one member of the group consisting enzymes, antigens, antibodies, lektins, haptens, nucleic acids, colors, metal compounds, Biotin, Avidin and transmitter molecules and the structure is used as a sensor membrane.

22. A deposition matrix comprising a structure comprising at least one membrane extending along a plane, curved, cylindrical or vesicular surface consisting essentially of at least one layer of identical protein containing molecules, which molecules are arranged to form a crystal lattice having a lattice constant of 1 to 50 nm with a layer thereon selected from the group consisting of metal, carbon, silicon oxides and plastic as well as mixtures thereof.

23. A matrix of claim 22 wherein the membrane has pores with a diameter of 0.5 to 40 nm.

24. A matrix of claim 23 acting as a carrier for molecules, other than the membrane constituting molecules.

25. A matrix of claim 24 wherein the other molecules are selected from the group consisting of enzymes, antigens, antibodies, lektins, haptens, nucleic acids, colors, metal compounds, Biotin, Avidin or transmitter molecules.

26. The matrix of claim 22 wherein the metal or plastic layer is deposited by sputter coating.

27. The matrix of claim 22 wherein the metal, silicon oxide or plastic layer is deposited by vapor deposit.

28. The matrix of claim 22 wherein the plastic layer is deposited by plasma-polymerization.

29. The matrix of claim 22 wherein the carbon layer is deposited by sublimation.

30. The matrix of claim 22 wherein the layer is deposited after immobilization of at least one member selected from the group of proteins, peptides, glycoproteins, glycopeptides, polysaccharides, oligosaccharides, sugars, lipids, lipopolysaccharides, enzymes, antigens, antibodies, lektins, haptens, nucleic acids, colors, metal compounds, transmitter molecules, Biotin, Avidin.

* * * * *